United States Patent
Akram et al.

Patent Number: 5,990,355
Date of Patent: *Nov. 23, 1999

[54] SUBSTITUTED DIAMINOPHENOLS, PROCESS FOR THEIR PREPARATION, AND HAIR DYES CONTAINING SUCH COMPOUNDS

[75] Inventors: Mustafa Akram, Hamburg; Wolfgang Wolff, Bargteheide; Andreas Bittner, Offenbach; Uwe Kobs, Oberhausen, all of Germany

[73] Assignee: Hans Schwarzkopf GmbH & Co. KG., Hamburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/943,161

[22] Filed: Oct. 3, 1997

Related U.S. Application Data

[63] Continuation of application No. 08/547,416, Oct. 25, 1995, Pat. No. 5,676,706.

[30] Foreign Application Priority Data

Oct. 27, 1994 [DE] Germany .............................. 44 38 129

[51] Int. Cl.⁶ ................................................. C07C 209/38
[52] U.S. Cl. ............................................................ 564/443
[58] Field of Search ............................................... 564/443

[56] References Cited

U.S. PATENT DOCUMENTS

| | | | |
|---|---|---|---|
| 3,134,721 | 5/1964 | Seemuller et al. | |
| 3,184,387 | 5/1965 | Seemuller et al. | 8/416 |
| 3,666,812 | 5/1972 | Kalopissis et al. | 3/574 |
| 3,738,799 | 6/1973 | Kalopissis et al. | 8/416 |
| 4,566,875 | 1/1986 | Grollier et al. | 8/406 |
| 4,985,955 | 1/1991 | Grollier et al. | 8/416 |
| 5,180,397 | 1/1993 | Grollier et al. | 8/416 |
| 5,387,718 | 2/1995 | Kohler et al. | 568/38 |
| 5,525,123 | 6/1996 | Lorenz et al. | 8/408 |

FOREIGN PATENT DOCUMENTS

| | | |
|---|---|---|
| 348783 | 10/1960 | Switzerland . |
| 1063979 | 4/1967 | United Kingdom . |

*Primary Examiner*—Brian M. Burn
*Attorney, Agent, or Firm*—Smith, Gambrell & Russell; Beveridge, DeGrandi Weilacher & Young

[57] ABSTRACT

Compounds of the formula (I) and their salts with inorganic and organic acids,

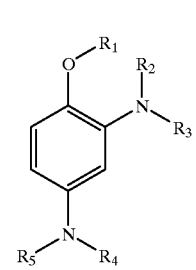

in which $R_1$ is a hydrogen atom or a trimethylsilyl group, $R_2$, $R_3$, $R_4$, and $R_5$ are, independently of each other, a hydrogen atom, a ($C_1$–$C_4$) alkyl group, a hydroxy-($C_2$–$C_3$) alkyl group, an alkoxy-($C_2$–$C_3$) group, an amino-($C_2$–$C_3$) group, or a 2,3-dihydroxypropyl group, and in which $R_1$, $R_2$, $R_3$, $R_4$ and $R_5$ are not simultaneously hydrogen atoms, and processes for their preparation and use as hair-coloring agents.

6 Claims, No Drawings

SUBSTITUTED DIAMINOPHENOLS, PROCESS FOR THEIR PREPARATION, AND HAIR DYES CONTAINING SUCH COMPOUNDS

This is a continuation of application Ser. No. 08/547,416 filed on Oct. 25, 1995 (now U.S. Pat. No. 5,676,706).

INTRODUCTION AND BACKGROUND

The present invention concerns new substituted 2,4-diaminophenols, processes for their preparation, and hair coloring agents containing such compounds.

So-called oxidative dyes are used extensively to color keratinic fibers because they produce intense dyes of high stability (fastness). Under the conditions of technical application (e.g., low dyeing temperature and short duration of dyeing) they yield intense colors with good stabilities. The dyes are formed in the dyeing process by oxidative coupling of a developer component and a coupler component. Such coupler and developer components for producing quite varied color tones, called hair dye intermediates in the following, are described often in the literature (K. Venkataraman, The Chemistry of Synthetic Dyes, Vol. V, Academic Press, 1971; F. Brody and M. S. Burns, J. Soc. Cosmet. Chem. (1968), volume 19, pages 361–379; H. Husemeyer, J. Soc. Cosmet. Chem. (1974), volume 25, pages 131–138).

Although the oxidative coupling, i.e., the development of the color, can in principle be done with oxygen from the air, in practice it usually goes too slowly or produces uneven colors. As a rule, then, chemical oxidizing agents are used. Oxidizing agents based on hydrogen peroxide are preferred. Along with hydrogen peroxide itself, addition compounds with urea, melamine or alkali perborate are also used.

For practical application as hair dyes, the hair dye intermediates are processed into a suitable cosmetic base which can, depending on the nature of the end product desired, be a solution, a cream, a foam (mousse) or a gel. This preparation is mixed with the oxidizing agent immediately before application to the hair.

As noted above, the oxidizing agent for color development can in principal also be oxygen from the air. However, experience teaches that the duration of color development or the temperatures required to shorten that time are too high for cosmetic use. No commercial product which comprises oxidation catalysts is known to the inventors.

Now it has been found, surprisingly, that such a hair coloring agent can be produced, in which, based on the usual foundation, the color-producing components are new substituted 2,4-diaminophenols of the general formula (I) or known couplers which react too slowly for air oxidation, which provide useful hair dyes through air oxidation on the hair by addition of a catalyst to the coloring material.

SUMMARY OF THE INVENTION

One object of the present invention is to provide substituted 2,4-diaminophenols of the formula (I) and their salts with inorganic and organic acids,

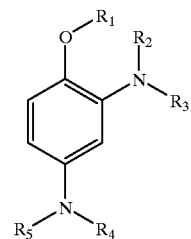

in which $R_1$ is a hydrogen atom or a trimethylsilyl group, $R_2$, $R_3$, $R_4$, and $R_5$ are, independently of each other, a hydrogen atom, a $(C_1-C_4)$ alkyl group, a hydroxy-$(C_2-C_3)$ alkyl group, an alkoxy-$(C_2-C_3)$ alkyl group, an amino-$(C_2-C_3)$ group, or a 2,3-dihydroxypropyl group, and in which $R_1$, $R_2$, $R_3$, $R_4$ and $R_5$ are not simultaneously hydrogen atoms.

Another object of the present invention is to provide processes for the preparation of such compounds.

Yet another object of the present invention is to provide hair-coloring agents based on compounds of the formula (I) in the form of a cream, solution, foam, or gel and which contain at least one compound of the formula (I) alone or with at least one developer, and an oxidation catalyst for formation of an oxidative dye by oxygen, whereby the oxidation catalyst comprises a transition metal salt or a transition metal complex, especially copper (II) chloride, sulfate, or acetate, alone or as the adduct with ammonia, ethylenediamine, phenanthroline, triphenylphosphine, 1,2-diphenylphosphinoethane, 1,3-diphenylphosphinopropane or amino acids individually or as a mixture, whereby the hair to be colored is treated particularly gently.

Another object is to provide a method for oxidative dyeing of hair which requires applying an effective oxidative dyeing amount of the composition described herein to hair.

Another object is to provide a component hair dyeing kit containing the substituted 2,4-diaminophenol of the formula (I), a developer, and optionally an oxidation catalyst.

DETAILED DESCRIPTION OF THE INVENTION

All known coupler and developer combinations are usable for the hair coloring agents (e.g., Examples 4, 5, 6, and 9) according to the present invention. Preferred couplers and developers are the following combinations:

1. p-toluylenediamine, resorcinol, m-aminophenol, 4-chlororesorcinol;
2. p-toluylenediamine, 2-methyl resorcinol, 4-chlororesorcinol, 2-amino-3-hydroxypyridine;
3. p-toluylenediamine, resorcinol, m-aminophenol, p-aminophenol, 2-hydroxy-4-aminotoluene;
4. 3-methyl-4-aminophenol, m-aminophenol, 2-hydroxy-4-aminotoluene, 2-amino-3-hydroxypyridine;
5. 3-methyl-4-aminophenol, 2-methylresorcinol, m-aminophenol, p-toluylenediamine, 2-hydroxy-4-aminotoluene, 2-amino-3-hydroxypyridine.

One especially preferred embodiment of the present invention is, therefore, a hair coloring agent based on oxidative dyes, characterized by 1. presence of a one-component hair coloring system,
2. lack of need to pretreat the hair with catalysts,
3. addition of a catalyst to the coloring mixture,
4. avoidance of hydrogen peroxide as the oxidizing agent, 5. use of known couplers not previously reactive to air oxidation,
6. use of new substituted 2,4-diaminophenols,
7. transition metal salts and transition metal complexes, especially copper (II) chloride, sulfate, or acetate, alone or as adducts with ammonia, 1,2-ethylenediamine, phenanthroline, triphenylphosphine, 1,2-diphenylphosphinoethane, 1,3-diphenylphosphinopropane, or amino acids such as glycine, leucine, methionine, alanine, phenylalanine and proline can be mentioned as catalysts for addition to the color mixture without any intent to limit catalysts to those mentioned.

The basic mixture for the hair coloring agent according to the present invention depends on the nature of the final product desired, e.g., a gel, a cream, a foam, or a solution containing surfactants. The mixture comprises components known from the state of the art and suitable for application to the hair in proportions usual for this purposes. The components of such mixtures are, for example, 1. Wetting and emulsifiying agents;
2. Thickeners;
3. Reducing agents;
4. Perfume oils;
5. Hair-care additives; and
6. Solvents, such as water or lower alcohols.

Dyeing hair with the coloring agent according to the present invention is accomplished by applying the components, which may or may not be diluted with water, onto the hair and distributing them. As is known to those skilled in the art, the proportion of hair coloring agent depends on the length of the hair to be dyed. The application temperatures are preferably in a range of 15° to 40° C. and the time of action is preferably between 4 and 45 minutes, especially 10 to 35 minutes. The hair coloring agent is then washed out, and, if desired, the hair is after-washed with a shampoo and rinsed again, and the hair is dried.

In comparison with the hair coloring agents known previously, the hair coloring agent according to the present invention is easier to use, milder, and better tolerated because the color development is through air oxidation in the presence of the catalyst which is an additive in the color mixture, and because hydrogen peroxide is not used. Thus, the hair coloring composition herein are free of hydrogen peroxide, though hydrogen peroxide may be added if desired. No impairment of the dyeing need be accepted.

In the preparation of the new substituted 2,4-diaminophenols, conversion of the compound of formula (IIa) or (IIb)

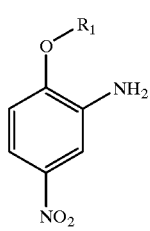

(IIa)

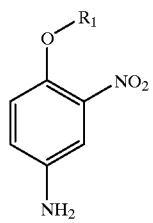

(IIb)

with a 2-chloroethyl chloroformate or 3-chloropropyl chloroformate is based on the known selective hydroxyalkylation of an amine with chloroalkyl chloroformate followed by basic treatment of the chloroalkyl carbamate (cf. Otto, J. Prakt. Chem. (1890), 44:15; R. Adams and J. B. Segur, J. Am. Chem. Soc. (1923), 45:785). J. S. Pierce and R. Adams, J. Am. Chem. Soc. (1923), 45:790, describe in detail the reaction of chloroalkyl chloroformates with primary aromatic amines. In order to produce compounds of the general formula (IIIa) or (IIIb) where n=2 or 3

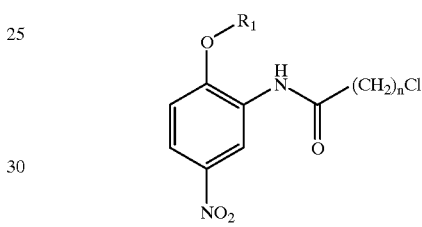

(IIIa)

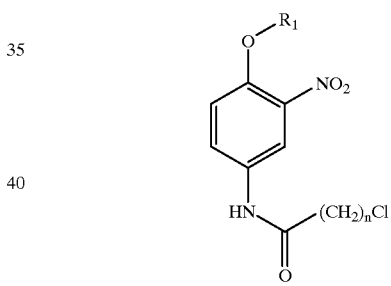

(IIIb)

the compound of formula (IIa) or (IIb) is put into an inert organic solvent (e.g., dioxane, $C_1$–$C_4$ alcohol, dimethylformamide, tetrahydrofuran, toluene, chlorobenzene, methyl ethyl ketone, 1,2-dimethoxyethane, methyl tert.-butyl ether or diethylene glycol dimethyl ether) and heated to a temperature between room temperature and reflux temperature, preferably between 30° C. and reflux temperature. Then an equimolar amount, or a slight excess, of one of the chloroalkyl chloroformates is added. The solvent can be combined with water if necessary. An acid-binding agent can be added with or in parallel with the previously mentioned chloroalkyl chloroformate. Acid-binding agents for this purpose include bases such as alkali hydroxides, bicarbonates or carbonates; alkaline earth oxides, hydroxides, bicarbonates and carbonates; and tertiary organic amines. The reaction proceeds from 1 to 12 hours.

After complete conversion, the carbamates are isolated by (a) chilling the reaction mixture by stirring it with water or ice or a mixture of ice and water, or (b) filtering off the inorganic salts and partially or completely distilling off the solvent, with cooling if desired, e.g., by addition of ice, so that the carbamates of formula (IIIa) or (IIIb) precipitate almost quantitatively.

The carbamates of the general formula (IIIa) or (IIIb) are converted into the hydroxyalkyl compounds of formula (IVa) or (IVb)

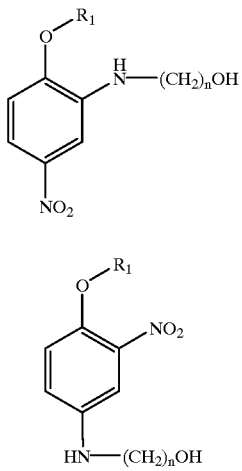

(IVa)

(IVb)

by treatment with strong base. Alkali or alkaline earth hydroxides are suitable; a solution of (10 to 50% sodium or potassium hydroxide by weight in water is preferably used. There are two practical ways of carrying out this process:

(a) The carbamate of formula (IIIa) or (IIIb) is put into water or an organic solvent, e.g., a $C_1$–$C_4$ alcohol, a water-miscible ether, or mixtures of those, at room temperature. Then approximately the calculated quantity of alkali, i.e., 4 moles of alkali per mole of carbamate, is added and the mixture is stirred until the conversion is complete. If necessary, the mixture can be heated to reflux or more alkali can be added.

(b) The alkali, which can be diluted with the solvents mentioned, is prepared. The carbamate with the general formula (IIIa) or (IIIb) is added in pure form, or dissolved in one of the organic solvents mentioned, at a temperature between room temperature and about 70° C. and the mixture is stirred until the conversion is complete.

In both variants the reaction solution, which has a pH of about 12 to 14, can be neutralized by addition of an organic or inorganic acid to a pH of about 5 to 10. Then the salt is separated, water is added if desired, and the product having the general formula (IVa) or (IVb) is isolated after removal of the organic solvent.

In both the processes above, the duration of the reaction is distinctly reduced by adding about 25 to 30% by weight of one of the organic solvents listed above to the aqueous reaction mixture, whereby the inorganic salts remain in solution in the reaction medium. About 1 to 12 hours is required for the conversion.

Compounds of the general formula (I) are prepared by reducing the compounds of the general formula (Va) or (Vb)

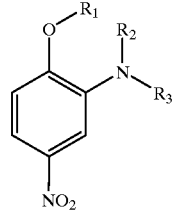

(Va)

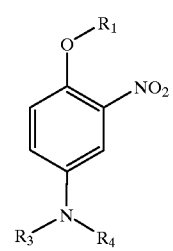

(Vb)

optionally after alkylation or alkoxylation, catalytically or with base metals. The usual catalysts such as Raney nickel, palladium on activated charcoal, or platinum on activated charcoal, are used in the catalytic reduction. The reaction temperature is between room temperature and 120° C., preferably between 35° and 100° C. The pressure is between normal pressure and 100 bar, preferably between 20 and 70 bar. The usual solvents such as water, toluene, acetic acid, lower alcohols or ether are used as solvents. After completion of the reduction and separation of the catalyst, the product of the general formula (I), optionally after alkylation or alkoxylation, can be isolated in the free form by removing the solvent under a protective gas. The well-known compounds, dimethyl sulfate and diethyl sulfate have proven to be good alkylating agents and ethylene oxide and propylene oxide have proven to be good alkoxylating agents. The product of the general formula (I) is preferably converted to a salt by adding an approximately equivalent quantity of an acid under a protective gas. The salt either precipitates immediately or can be obtained by removal of the solvent.

Suitable inorganic acids for forming the salt are, for example, hydrochloric acid, sulfuric acid, and phosphoric acid. Suitable organic acids are acetic acid, propionic acid, lactic acid or citric acid.

The following examples are intended to describe and explain the invention, without the invention being limited to the examples:

A. PREPARATION OF THE CATALYSTS

EXAMPLE A.1

Preparation of Copper(II) Glycinate 1.8 g (9.8 mmol) copper (II) acetate is dissolved in 100 ml hot methanol, and a solution of 1.5 g (20 mmol) glycine in 50 ml methanol is added with stirring. The solution becomes turbid due to precipitation of the product. Stirring is continued for two hours at a temperature causing precipitation. The precipitated product is filtered off and dried.

Yield: 2.49 g (96% of theoretical).

Melting point: >210° C.

EXAMPLE A.2

Preparation of Copper(II) 1,2-diaminoethane Chloride 26.9 g (160 mmol) copper (II) chloride is dissolved in 300 ml hot methanol, and a solution of 9.6 g (160 mmol)

1,2-diaminoethane in 100 ml methanol is added with stirring. The solution becomes turbid due to precipitation of the product. Stirring is continued for an hour under reflux. The mixture is allowed to cool with stirring. The precipitated product is filtered off and dried.

Yield: 12.5 g (40% of theoretical)

Melting point: >210° C.

B. PREPARATION OF NEW COUPLERS

All the compounds prepared have been characterized by infrared spectra or by infrared and $^1$H-NMR spectra.

EXAMPLE B.1

Preparation of 4-(2-hydroxyethylamino)-2-aminophenol

Step (a): Carbamates from the aminonitrophenols.

Preparation of 4-(2-chloroethoxycarbonylamino)-2-nitrophenol (BI.a): 87.3 g (0.5 mol) 4-amino-2-nitrophenol is dissolved in a mixture of 225 ml 1,2-dimethoxyethane and 25 ml water. 25 g (0.26 mol) $CaCO_3$ is added and the solution is heated to about 70° C. 71.5 g (0.5 mol) 2-chloroethyl chloroformate is added dropwise over a period of 30 minutes, and heating is continued for an hour. 312 g water and 312 g ice are added to the mixture, which is adjusted to a pH of 1±0.5 with concentrated hydrochloric acid. The precipitated product is filtered off with suction, washed twice with about 200 ml water, and dried in vacuum at 40° C.

Yield: 160 g (94% of theoretical)

Melting point: 116–117° C.

The compounds shown in Table 1 were prepared similarly. In Table 1, the example number is shown in Column 1, the aminophenol used in Column 2, and the chloroformic acid ester added in Column 3. The yield obtained and the melting point of the product are shown in Columns 4 and 5 respectively.

TABLE 1

Carbamates from aminophenols and chloroformic acid esters

| Example | -phenol | Chloro-formate | Yield [%] | M.p. [° C.] |
|---|---|---|---|---|
| B2.a | 4-amino-2-nitro | 3-chloro-propylester | 87 | 112–113 |
| B3.a | 2-amino-4-nitro | 2-chloroethyl ester | 97 | 190 |
| B4.a | 2-amino-4-nitro | 3-chloro-propylester | 91 | 157–159 |

Step (b)-Preparation of 4-(2-hydroxyethylamino)-2-nitrophenol (B1.b): 359 g 50% potassium hydroxide is mixed 150 ml water, and 160 g (0.5 mol) 4-(2-chloroethoxycarbonylamino)-2-aminophenol (Step a) is added. The mixture is stirred for three hours at 40° C. Then the pH is adjusted to 6 with acetic acid and the product is precipitated The damp product is recrystallized from 1,2-dimethoxyethane.

Yield: 182 g (92% of theoretical)

Melting point: 109–111° C.

The compounds listed in Table 2 were prepared similarly. In Table 2, Column 1 shows the example number, Column 2 the substituent obtained after the rearrangement of the carbamate used, and Column 3 the second substituent of the phenol. The yield obtained and the melting point of the product are shown in Columns 4 and 5 respectively.

TABLE 2

Hydroxyalkylaminonitrophenols from the corresponding carbamates

| Example | -amino- | -phenol | Yield [%] | M.p. [° C.] |
|---|---|---|---|---|
| B2.b | 4-(3-hydroxypropyl) | -2-nitro- | 97 | (oil) |
| B3.b | 2-(2-hydroxyethyl) | -4-nitro- | 92 | 109–111 |
| B4.b | 2-(3-hydroxypropyl) | -4-nitro- | 86 | 157–159 |

N-alkylation of the Aminonitrophenols from Step b)

Step (c): Preparation of 4-[bis(2-hydroxyethyl)-amino]-2-nitrophenol by ethoxylation (B5.c): 397 g (2 mol) 4-(2-hydroxyethylamino)-2-nitrophenol is added to a mixture of 1.6 liters of water and 1.1 liters of 1,2-dimethoxyethane. The system is closed with a bubble counter and heated with stirring to 60° C. Ethylene oxide is conducted into this solution so that no ethylene oxide escapes through the bubble counter. After 5 hours the temperature is increased to 85° C., 9.2 g activated charcoal and 4.6 g Celite are added, and stirring is continued for 15 minutes. Then the mixture is filtered with suction. The residue is washed with 100 ml of 1,2-dimethoxyethane/water (1:1 v/v). 500 ml of 1,2-dimethoxyethane is distilled off the solution. The product which precipitates is filtered off with suction and dried. (This product is obtained starting from 4-amino-2-nitrophenol according to this procedure.)

Yield: 260 g (54% of theoretical)

Melting point: 103–104° C.

The compounds listed in Table 3 are obtained in just the same manner.

TABLE 3

Ethoxylation products from the intermediate stage b) or from 4-amino-2-nitrophenol and 2-amino-4-nitrophenol

| Example | -amino- | -phenol | Yield [%] | M.p. [° C.] |
|---|---|---|---|---|
| B6.c | 4-(3-hydroxypropyl-2-hydroxyethyl) | -2-nitro- | 45.3 | 99–101 |
| B7.c | 2-(3-hydroxypropyl-2-hydroxyethyl) | -4-nitro- | 52.1 | 139–141 |
| B8.c | 2-bis-(2-hydroxyethyl)- | -4-nitro- | 26.8 | 141–143 |
| B9.c | 4-bis-(2-hydroxyethyl)- | -2-nitro- | — | — |

Preparation of 4-[(ethyl-2-hydroxyethyl)-amino]-2-nitrophenol (B10.c): 39.6 g (200 mmol) 4-(2-hydroxyethylamino)-2-nitrophenol is added to a mixture of 150 ml water and 15 ml 1,2-dimethoxyethane. 33.9 g (220 mmol) diethyl sulfate is added dropwise at an internal temperature of 60° C. so that the pH of the solution is maintained between 6 and 8 by simultaneous dropwise addition of 10% sodium hydroxide (ca. 62 ml). After complete reaction, the solution is filtered through a pleated filter and cooled with stirring to 5° C. The product is allowed to crystallize.

Yield: 29.1 g (64.1% of theoretical)

Melting point: 91–92° C.

The compounds listed in Table 4 are prepared similarly.

TABLE 4

Alkylation products from the intermediate stage b) or from 4-amino-2-nitrophenol and 2-amino-4-nitrophenol with dialkyl sulfate

| Example | -amino- | -phenol |
|---|---|---|
| B11.c | 4-(methyl-2-hydroxyethyl- | -2-nitro- |
| B12.c | 4-(methyl-3-hydroxypropyl- | -2-nitro- |
| B13.c | 4-(ethyl-3-hydroxypropyl- | -2-nitro- |
| B14.c | 2-(methyl-2-hydroxyethyl- | -4-nitro- |
| B15.c | 2-(methyl-3-hydroxypropyl- | -4-nitro |
| B16.c | 2-(ethyl-3-hydroxypropyl- | -4-nitro- |
| B17.c | 2-(methyl- | -4-nitro- |
| B18.c | 2-(ethyl- | -4-nitro- |
| B19.c | 4-(methyl- | -2-nitro- |
| B20.c | 4-(ethyl- | -2-nitro |

EXAMPLE B.21
Preparation of 2,4-dinitrophenoxy-trimethylsilane 46 g (250 mmol) 2,4-dinitrophenol and 25.3 g (250 mmol) triethylamine are dissolved in 175 ml 1,2-dimethoxyethane. 27.2 g (250 mmol) trimethylchlorosilane is added dropwise with stirring. After completion of the addition, the mixture is heated to reflux for two hours. Then the precipitated triethylammonium chloride is filtered off, and the solution is added dropwise to 700 ml water. The precipitated product is filtered off with suction, washed twice with about 200 ml water, and dried. This reaction can also be carried out with bis(trimethylsilyl)amine instead of trimethylchlorosilane.

Yield: 39.4 g (61.5% of theoretical)

Melting point: 106–107° C.

Step (d): Hydrogenation of the aminonitrophenols from Step b or c and Example B21.

Preparation of 4-(2-hydroxyethylamino)-2-aminophenol (B1.d): 450 ml methanol is placed in a 0.7 liter autoclave. 96 g (0.5 mol) 4-(2-hydroxyethylamino)-2-nitrophenol (Step b) is dissolved in it, and 5 g of 10% palladium on activated charcoal (Degussa) is added. After closing the autoclave and inerting with nitrogen, hydrogenation is carried out at a pressure of 20 bar and a temperature of 40–45° C. until about 11.5 liters of hydrogen (at 1 bar) has been absorbed. The warm solution is filtered through a G4 frit under nitrogen. 1.1 mol of 70% sulfuric acid is added dropwise, and the mixture is cooled with stirring. The precipitated product is filtered off with suction, washed with 70 ml methanol, and dried.

Yield: 81.5 g (60% of theoretical)

Melting point: >250° C.

The compounds listed in Table 5 are prepared similarly. Table 5 is read like those above.

TABLE 5

New couplers by hydrogenation of the intermediates from Steps b) or c)

| Example | -amino- | -phenol (sulfate) |
|---|---|---|
| B2.d | 4-(3-hydroxypropyl) | -2-amino- |
| B3.d | 2-(2-hydroxyethyl) | -4-amino- |
| B4.d | 2-(3-hydroxypropyl) | -4-amino- |
| B6.d | 4-(3-hydroxypropyl)-4-(2-hydroxyethyl) | -2-amino- |
| B7.d | 2-(3-hydroxypropyl)-2-(2-hydroxyethyl) | -4-amino- |
| B8.d | 2-(bis-2-hydroxyethyl) | -4-amino- |
| B9.d | 4-(bis-2-hydroxyethyl) | -2-amino- |
| B10.d | 4-(ethyl-2-hydroxyethyl) | -2-amino- |
| B11.d | 4-(methyl-2-hydroxyethyl) | -2-amino |
| B12.d | 4-(methyl-3-hydroxypropyl) | -2-amino |
| B13.d | 4-(ethyl-3-hydroxypropyl) | -2-amino- |
| B14.d | 2-(methyl-2-hydroxyethyl) | -4-amino- |
| B15.d | 2-(methyl-3-hydroxypropyl) | -4-amino- |
| B16.d | 2-(ethyl-3-hydroxypropyl) | -4-amino- |
| B21.d | O-trimethylsilyl-2- | -4-amino- |

C. EXAMPLE DYES

The hair coloring agents according to the present invention are aqueous agents. That is understood to mean all the agents that contain water in any way, such as creams, emulsions, gels, or even simple solutions. The hair coloring agent composition is a mixture of the coloring component with the usual additives for such cosmetic preparations. The usual additives in solutions, creams, emulsions or gels are, for example, solvents such as water; lower aliphatic alcohols such as ethanol, propanol and isopropanol; or glycols, alkylene glycols, glycerin, and glycol ethers, such as propylene glycol; as well as wetting agents or emulsifiers from the classes of anionic, cationic, amphoteric or nonionic surface-active substances such as fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides, and ethoxylated fatty acid esters; and thickeners such as higher fatty alcohols, starches, cellulose derivatives, Vaseline, paraffin oil and fatty acids. The ingredients mentioned are used in the proportions usual for such purposes. For instance, the wetting agents and emulsifiers are used at concentrations of about 0.5 to 30% by weight, while the preparations can contain thickeners at proportions of about 0.1 to 25% by weight.

The preparations can be mildly acidic, neutral or alkaline, depending on their compositions. In particular, they have a pH in the alkaline range between 7.5 and 11.5. Adjustment of the pH is preferably done with ammonia. However, organic amines such as monoethanolamine and triethanolamine can also be used, or even inorganic bases such as sodium hydroxide and potassium hydroxide.

In processes for oxidative dyeing of hair, the hair coloring agents of the present invention, which comprise a combination of known developer substances with at least one compound of the general formula I as a coupler substance and, if desired, other known coupler substances and directly absorbed dyes and, if desired, the previously mentioned catalysts, are applied to the hair. Optionally, the coloring agent can also be mixed with oxidizing agent before application.

Alternatively, the following hair-coloring agents, to which no oxidizing agent is added before or during use, are applied to on the hair: Hair coloring agents which produce an oxidative hair dye by air oxidation, in the form of a creme, solution, foam or gel comprising at least one coupler and at least one developer and, as the oxidation catalyst for air oxidation, copper (II) 1,2-diaminoethane chloride, copper (II) 1,10-phenanthroline chloride, copper (II) tetramine sulfate, or copper (II) glycinate, individually or as a mixture.

The content of catalyst is from 0.05 to 0.5 percent by weight based on the weight of the hair coloring agent.

The principal oxidizing agent for developing hair color is hydrogen peroxide, e.g., a 6% aqueous solution, and its addition compounds with urea, melamine or sodium borate, and mixtures of such hydrogen peroxide addition compounds with potassium peroxydisulfate.

The application temperatures vary in the range of 15° to 40° C. After about 10 minutes of action, the hair coloring agent is washed out of the hair to be dyed. After that the hair can be washed with a mild shampoo and dried.

The following examples are intended to explain better the subject of the invention without the invention being limited to them:

EXAMPLE 1

Hair Coloring Agent in Cream Form

| | |
|---|---|
| 2.20 g | p-toluylenediamine sulfate |
| 2.66 g | 4-(2-hydroxyethylamino)-2-aminophenol (as the sulfate) |
| 1.20 g | oleic acid |
| 0.50 g | sodium dithionite |
| 6.20 g | lauryl alcohol diglycol ether sulfate, sodium salt (28% solution) |
| 18.0 g | cetyl-stearyl alcohol |
| 7.50 g | ammonia, 25% |
| water | to make 100 g. |

40 g of the hair coloring agent described above is brushed into 100% gray hair. After acting for 10 minutes at room temperature the coloring agent is washed out and the hair is dried. The hair has taken on an even light to medium ash-blond hue.

EXAMPLE 2

Hair Coloring Agent in Gel Form

| | |
|---|---|
| 2.20 g | p-toluylenediamine sulfate |
| 2.66 g | 4-(2-hydroxyethylamino)-2-aminophenol (as the sulfate) |
| 12.0 g | oleic acid |
| 12.0 g | isopropanol |
| 5.00 g | Nonoxynol-4 |
| 10.0 g | ammonia, 25% |
| 0.5 g | sodium sulfite, anhydrous |
| water | to make 100 g. |

60 g of the coloring agent described above is mixed with 60 g of 6% hydrogen peroxide solution shortly before use. The mixture is allowed to act on 100% gray hair for 10 minutes at 35° C. Then the coloring substance is washed out, and the hair is shampooed and dried. The hair is colored in a medium blond hue.

EXAMPLE 3

Hair Coloring Agent in Cream Form

| | |
|---|---|
| 2.20 g | p-toluylenediamine sulfate |
| 2.66 g | 4-(2-hydroxyethylamino)-2-aminophenol (as the sulfate) |
| 1.20 g | oleic acid |
| 0.50 g | sodium dithionite |
| 6.20 g | lauryl alcohol diglycol ether sulfate, sodium salt (28% solution) |
| 18.0 g | cetyl-stearyl alcohol |
| 0.20 g | tetrammine copper sulfate |
| 7.50 g | ammonia, 25% |
| water | to make 100 g. |

40 g of the hair coloring agent described above is brushed into 100% gray hair. After acting for 10 minutes at room temperature, the coloring agent is washed out and the hair is dried. The hair has an even medium-blond matte color hue.

EXAMPLE 4

Hair Coloring Agent in Cream Form

| | |
|---|---|
| 2.20 g | p-toluylenediamine sulfate |
| 1.10 g | resorcinol |
| 1.20 g | oleic acid |
| 0.50 g | sodium dithionite |
| 6.20 g | lauryl alcohol diglycol ether sulfate, sodium salt (2.8% solution) |
| 18.0 g | cetyl-stearyl alcohol |
| 0.20 g | tetrammine copper sulfate |
| 7.50 g | ammonia, 25% |
| water | to make 100 g. |

40 g of the hair coloring agent described above is applied to 40% gray medium-blond hair. After acting for 15 minutes at room temperature, the coloring agent is washed out and the hair is dried. The hair has taken on an even golden-brown hue.

EXAMPLE 5

Hair Coloring Agent in Cream Form

| | |
|---|---|
| 2.20 g | p-toluylenediamine |
| 1.09 g | m-aminophenol |
| 0.01 g | HC Red No. 3 |
| 2.50 g | lauryl ether sulfate sodium salt (70% paste) |
| 1.00 g | oleic acid |
| 0.60 g | sodium sulfite, anhydrous |
| 12.0 g | cetyl alcohol |
| 6.00 g | myristyl alcohol |
| 1.00 g | propylene glycol |
| 0.20 g | copper (II) 1,2-ethylenediamine dichloride |
| 10.0 g | ammonia |
| water | to make 100 g. |

40 g of the hair coloring agent described above is applied to 70% gray medium blond hair. After acting for 12 minutes at room temperature, the coloring agent is washed off and the hair is dried. The hair has taken on an even light-blond hue with an ashy reflection.

EXAMPLE 6

Hair Coloring Agent in Cream Form

| | |
|---|---|
| 2.20 g | p-toluylenediamine |
| 1.23 g | p-amino-o-cresol |
| 0.01 g | HC Red No. 3 |
| 2.50 g | lauryl ether sulfate sodium salt (70% paste) |
| 1.00 g | oleic acid |
| 0.60 g | sodium sulfite, anhydrous |
| 12.0 g | cetyl alcohol |
| 6.00 g | myristyl alcohol |

-continued

| | |
|---|---|
| 1.00 g | propylene glycol |
| 0.20 g | copper (II) 1,10-phenanthroline dichloride |
| 10.0 g | ammonia, 25% |
| water | to make 100 g. |

40 g of the hair coloring agent described above is applied to naturally medium-blond hair. After acting for 12 minutes at room temperature, the coloring agent is washed off and the hair is dried. The hair has taken on an even dark blond violet hue.

EXAMPLE 7

Hair Coloring Agent in Cream Form

| | |
|---|---|
| 2.66 g | 4-(2-hydroxyethylamino)-2-aminophenol (as the sulfate) |
| 1.20 g | oleic acid |
| 0.50 g | sodium dithionite |
| 6.20 g | lauryl alcohol diglycol ether sulfate, sodium salt (28% solution) |
| 18.0 g | cetyl-stearyl alcohol |
| 7.50 g | ammonia, 25% |
| water | to make 100 g. |

40 g of the hair coloring agent described is applied to 100% naturally gray hair. After acting for 10, 20, and 30 minutes at room temperature, the coloring agent is washed off and the hair is dried. The hair has taken on an even reddish violet hue. The intensity of the color has developed in proportion to the residence time of the hair coloring agent.

EXAMPLE 8

Hair Coloring Agent in Cream Form

| | |
|---|---|
| 2.20 g | p-phenylenediamine sulfate |
| 6.20 g | 4-(2-hydroxyethylamino)-2-aminoanisole sulfate |
| 1.20 g | oleic acid |
| 0.50 g | sodium dithionite |
| 6.20 g | lauryl alcohol diglycol ether sulfate, sodium salt (28% solution) |
| 18.0 g | cetyl-stearyl alcohol |
| 0.20 g | copper (II) glycinate |
| 7.50 g | ammonia, 25% |
| water | to make 100 g. |

40 g of the hair coloring agent described above is applied to 100% naturally gray hair. After acting for 10 minutes at room temperature, the coloring agent is washed out and the hair is dried. The hair has taken on an even dark bluish-gray hue.

EXAMPLE 9

Hair Coloring Agent in Cream Form

| | |
|---|---|
| 2.66 g | 4-(2-hydroxylethylamino)-2-aminophenol (as the sulfate) |
| 1.20 g | oleic acid |
| 0.50 g | sodium dithionite |
| 6.20 g | lauryl alcohol diglycol ether sulfate, sodium salt (28% solution) |
| 18.0 g | cetyl-stearyl alcohol |
| 0.20 g | copper (II) glycinate |
| 7.50 g | ammonia, 25% |
| water | to make 100 g. |

40 g of the hair coloring agent described above is applied to 100% naturally gray hair. After acting for 10, 20 and 30 minutes at room temperature, the coloring agent is washed out and the hair is dried. The hair has taken on an even medium-blond hue with a violet reflection. The intensity of the color has developed corresponding to the residence time.

In general, the hair coloring agents are based on compounds of the general formula (I) in the form of a cream, solution, foam, or gel which contain at least one compound of the general formula (I) alone or with at least one developer, and an oxidation catalyst for formation of an oxidative dye by oxygen, whereby the oxidation catalyst comprises a transition metal salt or a transition metal complex, especially copper (II) chloride, sulfate, or acetate, alone or as the adduct with ammonia, ethylenediamine, phenanthroline, triphenylphosphine, 1,2-diphenylphosphinoethane, 1,3-diphenylphosphinopropane or amino acids individually or as a mixture, whereby the hair to be colored is treated particularly gently.

The hair dyes are based on compounds of the general formula (I) in the form of a cream, solution, foam, or gel comprising at least one compound of the general formula (I) alone or with a developer.

The hair coloring agent is based on compounds of the general formula (I) in the form of a cream, solution, foam or gel, comprising at least one compound of the general formula (I) alone or with at least one developer, which causes oxidative dyeing by addition of an oxidizing agent.

The hair dyes are based on compounds of the general formula (I) in the form of a creme, solution, foam or gel comprising at least one compound of the general formula (I) alone or with at least one developer, in which the oxidative dyeing is caused by addition of an oxidizing agent and an oxidation catalyst.

The hair dyes are based on compounds of the general formula (I) in the form of a cream, solution, foam or gel, comprising at least one compound of the general formula (I) in the absence of a developer.

The hair dyes are based on compounds of the general formula (I) in the form of a cream, solution, foam or gel comprising at least one compound of the general formula (I) alone or with at least one developer and an oxidation catalyst for production of an oxidative dye by air oxygen, in which the oxidation catalyst comprises a transition metal salt or transition metal complex, especially copper (II) chloride, sulfate, or acetate, alone or as an adduct with ammonia, ethylenediamine, phenanthroline, triphenylphosphine, 1,2-diphenylphosphinoethane, 1,3-diphenylphosphinopropane or amino acids, individually or as a mixture.

The hair coloring agents produce an oxidative hair dye by air oxidation and are in the form of a creme, solution, foam or gel comprising at least one coupler and at least one developer and, as the oxidation catalyst for air oxidation, copper (II) 1,2-diaminoethane chloride, copper (II) 1,10-phenanthroline chloride, copper (II) tetrammine sulfate, or copper (II) glycinate, individually or as a mixture. The content of catalyst is from 0.05 to 0.5 percent by weight, based on the weight of the hair coloring agent.

Further variations and modifications of the foregoing will be apparent to those skilled in the art and such variations and modifications are intended to be encompassed by the claims that are appended hereto.

German Priority Application P 44 38 129.8 filed on Oct. 27, 1994 is relied on and incorporated by reference in its entirety. U.S. Pat. No. 5,230,710 is incorporated by reference in its entirety.

We claim:

1. A compound of the formula (I) or its salts with an inorganic or organic acid,

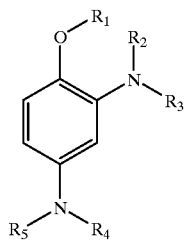
(I)

in which $R_1$ is a hydrogen atom, $R_2$, $R_3$, $R_4$, and $R_5$ are, independently of each other, a hydrogen atom or a hydroxy-$(C_2-C_3)$ alkyl group and in which $R_1$, $R_2$, $R_3$, $R_4$, and $R_5$, are not simultaneously hydrogen atoms.

2. The compound as defined in claim 1 wherein $R_1$, $R_2$, $R_3$, and $R_5$ are hydrogen atoms, and wherein $R_4$ is a hydroxy-$(C_2)$ alkyl group.

3. The compound as defined in claim 1 wherein $R_1$, $R_2$, $R_3$, and $R_5$ are hydrogen atoms, and wherein $R_4$ is a hydroxy-$(C_3)$ alkyl group.

4. The compound as defined in claim 1 wherein $R_1$, $R_3$, $R_4$, and $R_5$ are hydrogen atoms, and wherein $R_2$ is a hydroxy $(C_2)$ alkyl group.

5. The compound as defined in claim 1 wherein $R_1$, $R_3$, $R_4$, and $R_5$ are hydrogen atoms and wherein $R_2$ is a hydroxy $(C_3)$ alkyl group.

6. The compound as defined in claim 1 wherein $R_1$, $R_2$, and $R_3$ are hydrogen atoms, and wherein $R_4$ and $R_5$ are hydroxy $(C_2)$ alkyl groups.

* * * * *